(12) United States Patent
Hou

(10) Patent No.: US 12,390,531 B2
(45) Date of Patent: Aug. 19, 2025

(54) COLON-TARGETED ACTIVE AGENT DELIVERY CARRIER AND USES THEREOF

(71) Applicant: AWKEONOMIC BIOTECHNOLOGY CO., LTD., Taipei (TW)

(72) Inventor: Shih-Kuo Hou, Taipei (TW)

(73) Assignee: AWKEONOMIC BIOTECHNOLOGY CO., LTD., Taipei (TW)

( * ) Notice: Subject to any disclaimer, the term of this patent is extended or adjusted under 35 U.S.C. 154(b) by 0 days.

(21) Appl. No.: 18/792,077

(22) Filed: Aug. 1, 2024

(65) Prior Publication Data
US 2024/0390501 A1 Nov. 28, 2024

Related U.S. Application Data

(63) Continuation of application No. 18/367,279, filed on Sep. 12, 2023.

(30) Foreign Application Priority Data

Sep. 12, 2023 (TW) ................................ 112134692

(51) Int. Cl.
| | |
|---|---|
| A61K 47/36 | (2006.01) |
| A61K 9/00 | (2006.01) |
| A61K 9/107 | (2006.01) |
| A61K 9/14 | (2006.01) |
| A61P 5/50 | (2006.01) |

(52) U.S. Cl.
CPC ............ *A61K 47/36* (2013.01); *A61K 9/0053* (2013.01); *A61K 9/107* (2013.01); *A61K 9/146* (2013.01); *A61P 5/50* (2018.01)

(58) Field of Classification Search
None
See application file for complete search history.

(56) References Cited

U.S. PATENT DOCUMENTS

| | | | | |
|---|---|---|---|---|
| 3,862,332 A | * | 1/1975 | Barnhart | A61K 31/10 514/712 |
| 11,272,725 B2 | | 3/2022 | Hou | |
| 2002/0119941 A1 | * | 8/2002 | Ni | A61K 47/36 514/19.3 |

FOREIGN PATENT DOCUMENTS

| | | | | |
|---|---|---|---|---|
| TW | I717827 B | 2/2021 | | |
| WO | WO 2014/209865 A1 | 12/2014 | | |
| WO | WO-2022029242 A1 | * | 2/2022 | ............. A23D 7/003 |

OTHER PUBLICATIONS

Silva, C. M., Ribeiro, A. J., Figueiredo, M., Ferreira, D., & Veiga, F. (2005). Microencapsulation of hemoglobin in chitosan-coated alginate microspheres prepared by emulsification/internal gelation. The AAPS Journal, 7, E903-E913. (Year: 2005).*
Salunke et al., "Oral drug delivery strategies for development of poorly water soluble drugs in paediatric patient population," 2022, Advanced Drug Delivery Reviews 190, 23 pages.
FDA, "What Are "Biologics" Questions and Answers," 2018, 1 page.
Hill et al., "The International Scientific Association for Probiotics and Prebiotics consensus statement on the scope and appropriate use of the term probiotic," 2014, Nature, vol. 11, 9 pages.
Brown et al, "Materials for oral delivery of proteins and peptides," 2020, Nature, 22 pages.
Mantaj et al., "Recent advances in the oral delivery of biologics," 2020, The Pharmaceutical Journal, 7 pages.
Robert Langer, "Drug delivery and targeting," 1998, Nature, vol. 392, 7 pages.
Barbier et al., "The clinical progress of mRNA vaccines and immunotherapies," 2022, Nature, 15 pages.
Sioson et al., "Challenges in delivery systems for CRISPR-based genome editing and opportunities of nanomedicine," 2021, Biomedical Engineering Letters, 17 pages.
David J. Brayden, "The Centenary of the Discovery of Insulin: An Update on the Quest for Oral Delivery," 2021, Frontiers in Drug Delivery, 7 pages.
Tewabe et al., "Targeted Drug Delivery—From Magic Bullet to Nanomedicine: Principles, Challenges, and Future Perspectives," 2021, Journal of Multidisciplinary Healthcare, 14 pages.
Southwell et al., "Colonic transit studies: normal values for adults and children with comparison of radiological and scintigraphic methods," 2009, Pediatr Surg Int, 14 pages.
Varol et al., "Intestinal Lamina Propria Dendritic Cell Subsets Have Different Origin and Functions," 2009, Immunity, 11 pages.
Bernardo et al., "Chemokine(C—C Motif) Receptor 2 Mediates Dendritic Cell Recruitment to the Human Colon but Is Not Responsible for Differences Observed in Dendritic Cell Subsets, Phenotype, and Function Between the Proximal and Distal Colon," 2016, Cellular and Molecular Gastroenterology and Hepatology, 23 pages.
Chang et al., "Pattern of Stress-Induced Hyperglycemia according to Type of Diabetes: A Predator Stress Model," 2013, Diabetes & Metabolism Journal, 9 pages.
Hartini et al., "Microencapsulation of Curcumin in Crosslinked Jelly Fig Pectin Using Vacuum Spray Drying Technique for Effective Drug Delivery", 2012, Polymers, 18 pages.
Ponrasu et al., "Evaluation of jelly fig polysaccharide as a shell composite ingredient of colon-specific drug delivery", 2021, Journal of Drug Delieevery Science and Technology.
Koh et all, "Encapsulated Probiotics: Potential Techniques and Coating Materials for Non-Dairy Food Applications", 2022, Appl. Sci., 31 pages.
Jue Wang et al., "Dessecting the toxicological profile of polysorbate 80 (PS80): comparative analysis of constituent variability and biological impact using a zebrafish model", European Journal of Pharmaceutical Sciences vol. 200, Sep. 1, 2024, pp. 1-16.

(Continued)

*Primary Examiner* — Dale R Miller
(74) *Attorney, Agent, or Firm* — MUNCY, GEISSLER, OLDS & LOWE, P.C.

(57) ABSTRACT

A colon-targeted active agent delivery carrier includes a low methoxyl pectin derived from Jelly fig (Jelly fig LM pectin) and a divalent cation, wherein the Jelly fig LM pectin crosslinks with the divalent cation in an egg-box conformation, wherein the colon-targeted composition is degraded by at least one enzyme in the colon of the subject to release the active agent.

6 Claims, 9 Drawing Sheets
(6 of 9 Drawing Sheet(s) Filed in Color)

(56) References Cited

OTHER PUBLICATIONS

Guillemette Salomon et al., "Surfactant irritations and allergies", Eur J Dermatol, vol. 32, No. 6, Nov.-Dec. 2022; pp. 677-681.
Laury Sellem et al., "Food additive emulsifiers and cancer risk: Results from the French prospective NutriNet-Sante cohort", PLOS Medicine, Feb. 13, 2024, pp. 1-22.
Search report for the corresponding EP application No. 24171953.3, dated Oct. 16, 2024, 13 pages.
Lee J S et al: "Characteristics and antioxidant activity of catechin-loaded calcium pectinate gel beads prepared by internal gelation", Colloids and Surfaces B: Biointerfaces, vol. 74, No. 1 (Nov. 1, 2009), pp. 17-22.
Das Surajit: "Pectin based multi-particulate carriers for colon-specific delivery of therapeutic agents", International Journal of Pharmaceutics vol. 605, Jun. 17, 2021, 24 pages.
Sriamornsak Pornsak, "Application of pectin in oral drug delivery", Expert Opinion on Drug Delivery, Taylor & Francis, vol. 8, No. 8, May 13, 2011, 16 pages.

\* cited by examiner (A)

(B)

(A)

(B)

(A)

(B)

(A)           (B)

(A)

(B)

COLON-TARGETED ACTIVE AGENT DELIVERY CARRIER AND USES THEREOF

CROSS REFERENCE TO RELATED APPLICATIONS

This application is a Continuation of co-pending application Ser. No. 18/367,279, filed on Sep. 12, 2023, for which priority is claimed under 35 U.S.C. § 120; and this application claims priority of Application No. 112134692 filed in Taiwan on Sep. 12, 2023 under 35 U.S.C. § 119, the entire contents of which is hereby incorporated by reference.

FIELD OF THE INVENTION

The present disclosure relates to a colon-targeted active agent delivery carrier and uses thereof. More specifically, it involves a colon-targeted active agent delivery carrier comprising a low methoxyl pectin (LM pectin) derived from Jelly fig, and various applications of said carrier.

BACKGROUND OF THE INVENTION

Unlike intravenous injection, oral dosage forms experience issues of poor bioavailability caused by incomplete absorption and the hepatic first-pass effect, which metabolizes the drug in the liver, rendering it less active or inactive. Accordingly, oral dosage forms must be administered in higher doses to achieve effective bioavailability. As for techniques to improve the solubility of poorly soluble oral drugs, many challenges still remain (Salunke, 2022, *Oral drug delivery strategies for development of poorly water soluble drugs in paediatric patient population*).

Active pharmaceutical ingredient (API) may include biological products such as vaccines, blood and blood components, allergenics, somatic cells, genetic material, tissues, and recombinant therapeutic proteins and antibodies. Biologics can be composed of sugars, proteins, or nucleic acids or complex combinations of these substances, or may be living entities such as cells and tissues (FDA, *What Are "Biologics" Questions and Answers*). Probiotics are live microorganisms, which may also be classified as biologics. When administered in sufficient amounts, probiotics bring health benefits to the host (Hill, 2014, *NATURE, The International Scientific Association for Probiotics and Prebiotics consensus statement on the scope and appropriate use of the term probiotic*). API may be seriously damaged by mammalian gastric juice and digestive enzymes in the small intestine. Currently, API must be administered through non-gastrointestinal routes such as injection or infusion, to achieve immune or therapeutic effects (Brown, 2020, *NATURE, Materials for oral delivery of proteins and peptides*; Mantaj, 2020, *Recent advances in the oral delivery of biologics*). By encapsulating API in or attaching API to polymers or lipids, the safety and efficacy of the resultant drugs can be greatly enhanced. Therefore, it is anticipated that the innovation of a new carrier technique could lead to the development of novel therapies (Langer, 1998, *Drug delivery and targeting*).

There is increasing focus on the use of mRNA as a therapeutic vaccine to train the immune system to seek out and kill cancer cells. According to pathologists, the optimal timing of immunotherapy, gene therapy, and cell therapy (cytotherapy) is during carcinogenesis, specifically when successful screening of patient-specific neoantigens occurs. This aids in formulating strategies for the implementation of clinical treatment. Immunotherapy for both tumor-specific and individual patient-specific neoantigens remains a challenge within the current techniques (Barbier, 2022, *NATURE, The clinical progress of mRNA vaccines and immunotherapies*).

During the COVID-19 epidemic, mRNA vaccines administered by injection were based on lipid-based nanoparticles (LNPs) as delivery carriers. Currently, the mRNA vaccines administered through injection are not available globally due to limitations involving vaccination training and facility arrangements by numerous health care providers and institutions, as well as the logistical difficulties with cold chain storage and transportation. Therefore, the development of highly stable, orally administered mRNA vaccine with an extended shelf life poses a significant challenge for scientists today.

Despite the remarkable advances of CRISPR-based gene therapy, safe and efficient delivery of the CRISPR components to the target cell or organ is the main challenge for clinical translation, and thus its medical applications still remain limited (Sioson, 2021, *Challenges in delivery systems for CRISPR-based genome editing and opportunities of nanomedicine*).

On the other hand, over the course of a century, the need for improved oral insulin preparations remains unfulfilled, posing an ongoing challenge for diabetic patients. Currently, in the absence of reigniting Big Pharma's interest in revisiting this endeavor, insulin primarily serves as a proof-of-principle benchmark for oral macromolecule delivery technologies (Brayden, 2021, *The Centenary of the Discovery of Insulin: An Update on the Quest for Oral Delivery*).

For quite some time, scientists have been studying how to deliver drugs into the circulation system through non-invasive local administration (Langer, 1998, *Drug delivery and targeting*). Ideally, a drug-targeting complex is expected to be atoxic, nonimmunogenic, biochemically inert, biodegradable, biocompatible, and physicochemically stable in vivo and in vitro. It should also have a predictable and controllable pattern of drug release, be a reasonably simple, reproducible, and cost-effective preparation, be easily and readily eliminated from the body, and have minimal drug leakage during transit. Unfortunately, there has never been a drug or a drug delivery system that has directly reached the bodily target (Tewabe, 2021, *Targeted Drug Delivery—From Magic Bullet to Nanomedicine: Principles, Challenges, and Future Perspectives*).

In light of the above, there is a need for the development of novel hydrogel composite particles as an oral delivery platform in the colon-targeted active agent delivery system.

SUMMARY OF THE INVENTION

The present disclosure provides a colon-targeted active agent delivery carrier, including:
- a low methoxyl pectin derived from Jelly fig (Jelly fig LM pectin); and
- calcium ion, wherein the Jelly fig LM pectin crosslinks with the calcium ion in an egg-box conformation.

In some embodiments, the Jelly fig LM pectin has the characteristics of:
(1) an average molecular weight of at least 750,000 daltons;
(2) an esterification degree of about 31% or less; and
(3) a galacturonic acid content of at least 75% to about 90%.

In some embodiments, the colon-targeted active agent delivery carrier is water-insoluble. In some embodiments, the colon-targeted active agent delivery carrier is undegradable by digestive juice in the stomach or small intestine.

In some embodiments, the colon-targeted active agent delivery carrier is a plurality of wet particles having a size of about 20 μm to about 1,000 μm. Alternatively, in some embodiments, the colon-targeted active agent delivery carrier is a plurality of dry powder particles having a size of about 5 μm to about 100 μm.

The present disclosure further provides a colon-targeted composition, comprising:
  the colon-targeted active agent delivery carrier; and
  an active agent embedded in the colon-targeted active agent delivery carrier.

In some embodiments, a dry weight ratio of the Jelly fig LM pectin to the active agent is about 1:1 to about 2,000:1.

In some embodiments, the active agent is selected from the group consisting of nucleic acids, peptides, proteins, therapeutic agents, diagnostic agents, non-biological materials, and combinations thereof. In some embodiments, the active agent is blood or blood components, an allergen, a cell, or a tissue. In some embodiments, is a somatic cell, a probiotic, a chimeric antigen receptor T cell, insulin, or a CRISPR/Cas polynucleotide. In some embodiments, the colon-targeted composition is a dietary supplement, a vaccine, a pharmaceutical composition, a diagnostic composition or a transfection reagent.

In some embodiments, the colon-targeted composition further includes an adjuvant.

In some embodiments, the colon-targeted composition is a plurality of particles having a size of about 20 μm to about 1,000 μm. Alternatively, in some embodiments, the colon-targeted composition is a plurality of particles having a size of about 5 μm to about 100 μm.

The present disclosure further provides a method for delivering an active agent to the colon of a subject, comprising administering the colon-targeted composition to the subject.

In some embodiments, the method is through oral administration.

In some embodiments, the colon-targeted composition is degraded by at least one enzyme in the colon of the subject to release the active agent. In some embodiments, the active agent is released at a constant rate.

In some embodiments, the subject is a mammal.

The present disclosure further provides a method for manufacturing the colon-targeted composition, including:
  (a) providing an aqueous phase including the LM pectin, the active agent and an insoluble salt of calcium;
  (b) mixing the aqueous phase with an oil phase to form a water-in-oil emulsion (w/o emulsion);
  (c) dripping an acid into the w/o emulsion, such that the insoluble salt of calcium dissolves to release calcium ion, and the LM pectin crosslinks with calcium ion to form hydrogel composite particles containing the active agent;
  (d) slowly pouring a critical volume of an aqueous solution containing soluble salt of calcium into the w/o emulsion to solidify the hydrogel composite particles and to separate the w/o emulsion into the aqueous phase and the oil phase, wherein the hydrogel composite particles are in the aqueous phase; and
  (e) separating the hydrogel composite particles from the aqueous phase.

In some embodiments, (a) includes:
  (a1) providing a solution containing the LM pectin derived from Jelly fig and the active agent, wherein the solution has a pH of about 6 to about 8; and
  (a2) mixing a suspension containing calcium carbonate with the solution of (a1).

In some embodiments, the oil phase in (b) is selected from the group consisting of canola oil, corn oil, peanut oil, sunflower oil, soybean oil, olive oil, linseed oil and palm oil.

In some embodiments, the acid in (c) is selected from the group consisting of acetic acid, citric acid, phosphoric acid, hydrochloric acid and nitric acid.

In some embodiments, the method further includes:
  (f) washing the hydrogel composite particles.

In some embodiments, in (f), the hydrogel composite particles are washed by the solution containing the soluble salt of calcium.

In some embodiments, the method further includes:
  (g) drying the hydrogel composite particles.

In some embodiments, the present disclosure further provides use of a low methoxyl pectin derived from Jelly fig (Jelly fig LM pectin) and calcium ion in the manufacture of a colon-targeted active agent delivery carrier.

In some embodiments, the present disclosure further provides use of the aforementioned colon-targeted active agent delivery carrier and an active agent in the manufacture of a colon-targeted composition.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
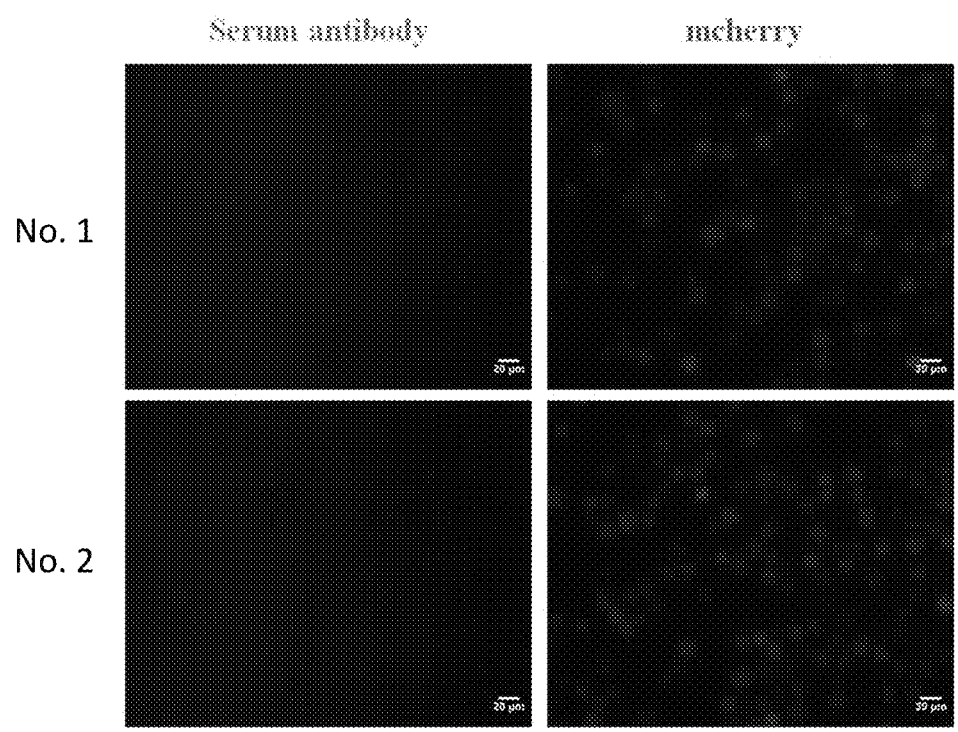
FIG. 1 shows the immunofluorescence assay (IFA) of serum from two mice at the age of 8 weeks and before oral vaccination.

Unless otherwise defined, all technical and scientific terms used herein have the same meaning as commonly understood by one of ordinary skill in the art to which this disclosure pertains. In the case of conflict, the present document, including definitions, will control. As used in this specification and the appended claims, the singular forms "a," "an" and "the" include plural references unless the content clearly dictates otherwise.

Throughout this specification, unless the context requires otherwise, the word "comprise" or "include," or variations such as "comprises," "comprising," "includes," or "including" will be understood to imply the inclusion of a stated element or integer or group of elements or integers but not the exclusion of any other element or integer or group of elements or integers.

Colon-Targeted Active Agent Delivery Carrier

The present disclosure provides a colon-targeted active agent delivery carrier that is water-insoluble calcium pectinate/pectate hydrogel particles, wherein the Jelly fig LM pectin is crosslinked with calcium ions forming a three-dimensional "egg box" network structure of polymeric hydrogel as a composite matrix. The colon-targeted active agent delivery carrier is capable of avoiding the release of active agent in the stomach, duodenum, jejunum and ileum, but delivers the active agent to the colon of the patient directly and releases it in the colon via an appropriate method. In this way, the local concentration of the active agent in the colon will be increased, so that the active agent could be absorbed and fulfill its role in treatment and healthcare. Meanwhile, the release of the active agent in the stomach and small intestine is avoided, so that adverse reactions will be reduced and bioavailability of the active agent, which is easily destroyed by gastric acid or metabolized by pepsin or pancreatic enzymes, will be improved.

In some embodiments, the present disclosure provides a colon-targeted active agent delivery carrier, including:
- a low methoxyl pectin derived from Jelly fig (Jelly fig LM pectin); and
- calcium ion, wherein the Jelly fig LM pectin crosslinks with the calcium ion in an egg-box conformation.

The term "carrier" refers to a substrate used in the process of active agent delivery in a subject, which serves to improve the selectivity, effectiveness, and/or safety of administration of active agents. The carrier may be used to control the release of active agents into systemic circulation. This can be accomplished either by slow release of active agents over a long period of time, or by triggered release at the target of active agents by some stimuli, such as changes in pH, application of heat, activation by light, and degradation by enzymes. The carrier may also be used to improve the pharmacokinetic properties, specifically the bioavailability, of active agents with poor water solubility and/or membrane permeability.

The Jelly fig LM pectin is calcium-sensitive due to its block-wise distribution of free carboxyl groups, which provides excellent properties of gel strength and biocompatibility.

The term "Jelly fig" may refer to the indigenous fruit in Taiwan of the *Ficus pumila* var. *awkeotsang*.

In some embodiments, the Jelly fig LM pectin has the characteristics of:
(1) an average molecular weight of at least 750,000 daltons;
(2) an esterification degree of about 31% or less; and
(3) a galacturonic acid content of at least 75% to about 90%.

The applicant surprisingly found that by using the calcium-sensitive LM pectin derived from Jelly fig, its calcium ion-crosslinked pectinate/pectate hydrogel provides excellent properties of encapsulation efficiency, biocompatibility, physicochemical stability due to its block-wise distribution of free carboxyl groups, and its final biodegradation of the delivery carrier matrix by colonic coordinated enzymes of gut microbiota for colon-targeting release.

In some embodiments, the LM pectin is derived from female syconium of Jelly fig, particularly from its achenes, pedicels, and sepals as a collective source of pectin raw materials. The Jelly fig LM pectin is obtained by the method of one-step anticoagulant water extraction, wherein the endogenous high methoxyl pectin (HM pectin) is deesterified by the endogenous pectin methylesterases during their synchronic extraction process. For example, the Jelly fig LM pectin may be prepared through the following steps:
(a) providing pectin raw materials from female syconium of Jelly fig, particularly its achenes, pedicels, and sepals as a whole;
(b) providing an anticoagulation extraction solution including sodium citrate, an organic acid and pure water, in which sodium citrate is added as an anticoagulation agent and the organic acid is added to adjust the pH value of the anticoagulation extraction solution to about 6 to about 8;
(c) extracting the Jelly fig raw materials with the anticoagulation extraction solution at a temperature of about 20° C. to about 50° C. to obtain a crude aqueous extract of Jelly fig LM pectin; and
(d) centrifuging the crude aqueous extract of Jelly fig LM pectin to collect supernatant, then precipitating the Jelly fig LM pectin by organic solvent.

The preparation of the Jelly fig LM pectin may be similar to or the same as those disclosed in U.S. Pat. No. 11,272,725 B2, which is incorporated herein by reference in its entirety.

Since the LM pectin derived from Jelly fig (Jelly fig LM pectin) is calcium-sensitive due to its block-wise distribution of free carboxyl groups, the Jelly fig LM pectin can be crosslinked with the divalent cation into a structural entity of water-insoluble calcium pectinate/pectate hydrogel in the egg-box conformation. Accordingly, this entity of water-insoluble calcium pectinate/pectate hydrogel matrix as a delivery carrier can embed and protect active agent(s) when they pass through the stomach and small intestine, and can be degraded by colonic bacterial enzymes (e.g., pectinase), allowing embedded active agent(s) to be released; thus, there is potential for it to be used as a colon-targeted active agent delivery carrier. On the contrary, due to random deesterification, commercially available LM pectin, which is usually produced from the traditional deesterification processes by modification of high methoxyl pectin, cannot crosslink with calcium ion due to random deesterification, and thus is not capable of qualifying as a matrix material of an active agent delivery carrier.

Due to the block-wise distribution of free carboxyl groups on backbone chains of the Jelly fig LM pectin, which demonstrates calcium-sensitive properties, it can be readily used to prepare the novel calcium pectinate/pectate hydrogel with "egg-box" model structure by calcium ion-crosslinking. This novel calcium pectinate/pectate hydrogel has excellent properties of biocompatibility, physicochemical stability, and the specific biodegradability by colonic coordinated enzymes; hence, it is capable of being used in preparation of a colon-targeting carrier for oral active agent delivery, maintaining its integrity while passing through the stomach and small intestine for site-specific release in the colon segment. On the contrary, commercially available LM pectins are usually produced from the traditional deesterification processes of HM pectin mainly derived from citrus peels and apple pomaces (reference to the prior art in U.S. Pat. No. 11,272,725 B2). The commercially available LM pectins (amidated or non-amidated) have weak gelation strength by van der Waals force and/or coupling reaction, and are incapable of forming the "egg-box" model network structure in preparation of a colon-targeting carrier for oral active agent delivery, due to their random deesterification without block-wise distribution of free carboxyl groups on backbone chains.

According to the above, in some embodiments, the colon-targeted active agent delivery carrier is water-insoluble. In some embodiments, the colon-targeted active agent delivery carrier is undegradable by digestive juice in the stomach or small intestine.

The colon-targeted active agent delivery carrier may be provided in any shape or size for carrying active agents. For example, the colon-targeted active agent delivery carrier may be provided in the form of solid particles or microspheres. Alternatively, the colon-targeted active agent delivery carrier may be provided in the form of shells of hard or soft capsules.

In some embodiments, the colon-targeted active agent delivery carrier may be provided in the form of particles. The colon-targeted active agent delivery carrier may include water or moisture, such that the particles are hydrogel particles. In some embodiments, the water or moisture may be removed, such that the hydrogel particles form dry powder. In some embodiments, the colon-targeted active agent delivery carrier is a plurality of wet particles having a size of about 20 μm to about 1,000 μm (e.g., in the form of hydrogel particles). In some embodiments, the colon-targeted active agent delivery carrier is a plurality of dry powder particles having a size of about 5 μm to about 100 μm, which may be formed by drying of the hydrogel particles. In some embodiments, the term "size" may refer to the largest dimension of the particles, or the diameter of the particles.

Colon-Targeted Composition

The present disclosure further provides a colon-targeted composition, wherein the active agent is embedded in the aforementioned "egg box" network structure through a sol-gel process.

The present disclosure further provides a colon-targeted composition, including:
  the colon-targeted active agent delivery carrier; and
  an active agent embedded in the colon-targeted active agent delivery carrier.

The term "active agent" may refer to an agent which is pharmacologically active.

The term "embedded" is used to describe that the active agent is at least partially covered or sheltered by the colon-targeted active agent delivery carrier. For example, the active agent may include a portion covered or sheltered by the colon-targeted active agent delivery carrier, while another portion of the active agent is exposed on a surface of the colon-targeted composition. Alternatively, the active agent may be completely covered or encapsulated by the colon-targeted active agent delivery carrier. For example, the active agent and the colon-targeted composition may jointly form solid particles, while the active agent may be substantially uniformly distributed in the particles and exposed on the surface of the particles. Alternatively, the colon-targeted composition may be provided as a capsule, with the colon-targeted active agent delivery carrier forming a shell of the capsule, and the active agent being encapsulated in the shell.

In some embodiments, the active agent may be selected from the group consisting of nucleic acids, peptides, proteins, therapeutic agents, diagnostic agents, non-biological materials, and combinations thereof. The therapeutic agent may be any physiologically or pharmacologically active substance that can produce a desired biological effect. The therapeutic agent may be a chemotherapeutic agent, an immunosuppressive agent, a cytokine, a cytotoxic agent, a nucleolytic compound, an anti-inflammatory compound, or a pro-drug enzyme, which may be naturally occurring, or produced by synthetic or recombinant methods, or by a combination thereof. In some embodiments, the active agent is blood or blood components, an allergen, a cell, or a tissue. In some embodiments, the active agent is a somatic cell, a probiotic, a chimeric antigen receptor T cell, insulin, or a CRISPR/Cas polynucleotide.

In some embodiments, according to the content of the active agent, the colon-targeted composition may be a dietary supplement, a vaccine, a pharmaceutical composition, a diagnostic composition or a transfection reagent. As for the dietary supplement, the colon-targeted composition may be used as or added into a food composition (i.e., edible food or drink or precursors thereof) in the manufacturing process thereof. Almost all food compositions can be supplemented with the colon-targeted composition of the present disclosure. The food compositions that can be supplemented with the colon-targeted composition of the present disclosure include, but are not limited to, candies, baked goods, ice creams, dairy products, sweet and flavor snacks, snack bars, meal replacement products, fast foods, soups, pastas, noodles, canned foods, frozen foods, dried foods, refrigerated foods, oils and fats, baby foods, or soft foods painted on breads, or mixtures thereof.

In some embodiments, the colon-targeted composition further includes an adjuvant. As used herein, the term "adjuvant" refers to a substance capable of eliciting an immune response in a subject exposed to the adjuvant.

In some embodiments, for preparation of colon-targeted active agent delivery carrier, the dry weight ratio of the Jelly fig LM pectin to the active agent is about 1:1 to about 2,000:1 (e.g., Pectin:mRNA=333:1; Pectin:DNA=150:1). This ratio range may provide better structural strength and/or stability of the colon-targeted composition.

In some embodiments, the colon-targeted composition may be provided in the form of particles. The colon-targeted composition may include water or moisture, such that the particles are hydrogel particles. In some embodiments, the water or moisture may be removed, such that the hydrogel particles form dry powder. In some embodiments, the colon-targeted composition is a plurality of particles having a size of about 20 μm to about 1,000 μm (e.g., in the form of hydrogel particles). In some embodiments, the colon-targeted composition is a plurality of particles having a size of about 5 μm to about 100 μm (e.g., in the form of powder).

Method for Delivering an Active Agent to the Colon of a Subject

The present disclosure further provides a medication administration route for delivering an active agent to the colon of a subject. Through the given administering pathway, the composite matrix is degraded and the active agent is released.

The present disclosure further provides a method for delivering an active agent to the colon of a subject, including administering the colon-targeted composition to the subject.

In some embodiments, the terms "subject" may refer to a mammal, including, but not limited to, murines (rats, mice), non-human primates, humans, canines, felines, ungulates (e.g., equines, bovines, ovines, porcines, caprines), etc.

In some embodiments, the colon-targeted composition may be administered in an effective amount to the subject. The term "effective amount" refers to the amount of the colon-targeted composition that, when administered to the subject, is sufficient to achieve an effective bioavailability or produce a desired biological effect in the subject.

In some embodiments, the colon-targeted composition is administered to the subject through oral administration. Alternatively, the colon-targeted composition may be administered to the gastrointestinal tract of the subject through injection.

As described in the above, the Jelly fig LM pectin matrix in the egg-box conformation can pass through the stomach and small intestine, and can be degraded by colonic bacterial enzymes (e.g., pectinase). That is, the colon-targeted composition is degraded by at least one enzyme in the colon of the subject to release the active agent. In some embodiments, the active agent may be released at a constant rate for at least a period of time, such as 1, 2, 3, 4 hours or more.

As described in the above, the novel calcium pectinate/pectate hydrogel carrier with "egg-box" model structure in calcium ion-crosslinked can pass through the stomach and small intestine, and maintain its integrity when delivering the loaded active agent to the targeted colon for release under the biodegradation of specific colonic bacterial coordinated enzymes (e.g., pectate lyase, pectinase). In some embodiments, the loaded active agent may be released at a constant rate in the colon for a period of time, such as 20 to 56 hours for humans under normal conditions (Southwell, 2009, *Colonic transit studies: normal values for adults and children with comparison of radiological and scintigraphic methods*) or even to 3 days or more in cases involving constipation.

Method for Manufacturing the Colon-Targeted Composition

The present disclosure further provides a method for manufacturing the colon-targeted composition, including:
(a) providing an aqueous phase including the Jelly fig LM pectin, the active agent and an insoluble salt of calcium;
(b) mixing the aqueous phase with an oil phase to form a water-in-oil emulsion (w/o emulsion);
(c) dripping an acid into the w/o emulsion, such that the insoluble salt of calcium dissolves to release calcium ion, and the Jelly fig LM pectin crosslinks with calcium ion to form hydrogel composite particles containing the active agent;
(d) slowly pouring a critical volume of a solution containing a soluble salt of calcium into the w/o emulsion to solidify the hydrogel composite particles and to separate the w/o emulsion into the aqueous phase and the oil phase, wherein the hydrogel composite particles are in the aqueous phase; and
(e) separating the hydrogel composite particles from the aqueous phase.

In the step (a), the Jelly fig LM pectin, the active agent and calcium carbonate may be dissolved or suspended in water to form the aqueous phase, which may be a solution or a suspension. The Jelly fig LM pectin, the active agent and calcium carbonate may be added to water at the same time. Alternatively, the Jelly fig LM pectin, the active agent and calcium carbonate may be added to water separately to form solutions or suspensions, and then the solutions or suspensions are mixed to form the aqueous phase.

In some embodiments, the term "insoluble salt" refers to a salt having a solubility in water less than about 1 g/L or less, such as less than about 0.1 g/L. For example, the insoluble salt of calcium includes, but is not limited to, calcium fluoride, calcium carbonate, calcium phosphate, calcium oxalate, calcium L-tartrate, calcium citrate, etc. Preferably, the insoluble salt is calcium carbonate.

In some embodiments, the term "soluble salt" refers to a salt having a solubility in water of about 1 g/L or more, such as 100 g/L or more. For example the soluble salt of calcium includes, but is not limited to, calcium chloride, calcium iodide, calcium hydroxide, calcium sulfate, calcium nitrate, etc. Preferably, the soluble salt of calcium is calcium chloride.

In some embodiments, the step (a) may include:
(a1) providing a solution containing the Jelly fig LM pectin derived from Jelly fig and the active agent, wherein the first solution has a pH of about 7.5; and
(a2) mixing a suspension containing calcium carbonate with the solution of (a1).

The Jelly fig LM pectin may be dissolved in water to form the first solution. In some embodiments, an acid or a base may be added to adjust the pH value to about 7.5. The second solution may be prepared by suspending calcium carbonate in water. In some embodiments, the active agent may also be dissolved or suspended in water before mixing with the first and second solutions. Then, the active agent (or the solution or suspension of the active agent) and the second solution are mixed with the first solution, thus forming the aqueous solution. In some embodiments, the first solution may be added into the second solution, and then the active agent (or the solution or suspension of the active agent) may be added into the mixture. In some embodiments, the active agent may be dissolved or suspended in the first solution or in the second solution.

In the step (b), the aqueous phase may be added into the oil phase, and the mixture may be stirred for a sufficient time period (e.g., 15 minutes) to form the w/o emulsion. The oil phase in the step (b) may be any oil that does not react with calcium carbonate and the active agent. The oil phase may be vegetable oils or animal oils. For example, the oil phase may be canola oil, corn oil, peanut oil, sunflower oil, soybean oil, olive oil, linseed oil, palm oil, and any combination thereof. Preferably, the oil phase consists only one kind of oil, or an oil from a single source.

In the step (c), the acid (may be provided in the form of an acid solution or may be mixed with an oil of the oil phase)

may be dripped into the w/o emulsion under stirring. The addition of acid decreases the pH value of the w/o emulsion. At a pH range of about 3 to 6, calcium carbonate dissolves in water to release calcium ion. The Jelly fig LM pectin crosslinks with calcium ion to form hydrogel composite particles containing the active agent. The acid in the step (c) may be any acidic compound that does not form an insoluble salt with calcium ion or the active agent. For example, the acid may be acetic acid, citric acid, phosphoric acid, hydrochloric acid, nitric acid, and any combination thereof. Preferably, the oil phase consists of only one kind of acid.

In the step (c), the insoluble salt of calcium suspended in the droplets dissolves in water to release calcium ions. Accordingly, the Jelly fig LM pectin cross-links with calcium ions to form the hydrogel particles of the three-dimensional "egg box" network structure through the ion-crosslinking sol-gel process, and the active agent is embedded therein.

In the step (d), the calcium chloride solution is slowly poured into the w/o emulsion under stirring. In some embodiments, the calcium chloride solution may be dripped into the w/o emulsion. The calcium ion from the calcium chloride solution solidifies the hydrogel composite particles. When the calcium chloride solution reaches the critical volume which induces phase separation, the w/o emulsion is separated into two layers of the aqueous phase (e.g., lower layer) and the oil phase (e.g., upper layer). The upper layer is the oil phase, and the lower layer is the aqueous phase containing the hydrogel composite particles.

Then, the oil phase (the upper layer) may be removed by decantation. The aqueous phase may be centrifuged to precipitate the hydrogel composite particles. The supernatant may be removed to obtain the hydrogel composite particles.

In some embodiments, the method further includes: (f) washing the hydrogel composite particles. In some embodiments, in the step (f), the hydrogel composite particles are washed by the solution containing the soluble salt of calcium. For example, the hydrogel composite particles may be washed three times with the solution containing calcium chloride. The hydrogel composite particles may be filtered through a filter (pore size of 0.45 μm) to remove the residual washing solution.

In some embodiments, the method further includes: (g) drying the hydrogel composite particles. For example, the hydrogel composite particles may be freeze-dried (lyophilization) to form powder.

The composite matrix of the colon-targeted active agent delivery carrier of the present disclosure has the following advantages:

(1) The colon-targeted active agent delivery carrier can deliver the loaded active agent to the targeted colon in integrity for release under the specific biodegradation of colonic coordinated pectic enzymes (e.g., pectate lyase, pectinase) of commensal bacteria.

(2) The active agent released in colon mucosa can be delivered to the targeted sites by an active or passive transport strategy, including:

(2a) The colonic intestinal immune system maintains tolerance to harmless food antigens and commensal microorganisms, yet robustly responds to harmful pathogens and other stimuli. Colonic lamina propria dendritic cells (colonic lpDCs) penetrate epithelial tight junctions to sense and sample the gut lumen content, and via endocytosis presented to T cells for cell-mediated immune and/or tolerance responses, or gene therapy (Varol, 2009, *Intestinal Lamina Propria Dendritic Cell Subsets Have Different Origin and Functions*; Bernardo, 2016, *Chemokine (C-C Motif) Receptor 2 Mediates Dendritic Cell Recruitment to the Human Colon but Is Not Responsible for Differences Observed in Dendritic Cell Subsets, Phenotype, and Function Between the Proximal and Distal Colon*).

(2b) Water-soluble active pharmaceutical ingredients (API), such as insulin, released in colon mucosa produce systemic effects through the blood circulation pathway of the hepatic portal vein and liver.

(2c) Although non-water soluble proteins and macromolecular substances released in colon mucosa, such as lipophilic antitumor-active substances, cannot be directly transported into the blood stream through capillaries for systemic effects, this can be done indirectly via the pathway of lymphatic vessels.

(2d) The API released in colon mucosa can be used in situ topical treatment for most types of colon polyps, adenocarcinoma, inflammation, and inflammatory bowel disease (IBD) such as Crohn's disease (CD) and Ulcerative Colitis (UC).

(2e) Adsorbent (e.g., DAV132) released in colon mucosa may exclude residual antibiotics accumulated in the colon under long-term intravenous antibiotic therapy in patients.

(2f) Dietary supplement, such as prebiotics, released in colon mucosa may help maintain or improve intestinal microbiota homeostasis.

(2g) Enzymolyzates, such as oligogalacturonates produced in colon mucosa from the specific biodegradation of calcium pectinate/pectate matrix by colonic coordinated pectic enzymes (e.g., pectate lyase, pectinase), are prebiotics that are the carbon and energy source required by the intestinal microbiota; and their metabolite butyrate may promote cell proliferation and epithelial growth, which in turn increases the thickness of the mucosa and enhances the intestinal barrier.

Regarding the colon-targeted active agent delivery carrier of the present disclosure, both wet and powder particles as the carrier for the active agent have the following characteristics:

(1) with active agent embedded inside, the composite matrix (carrier) can pass through the stomach and small intestine without being digested, and reach the colon almost integrally;

(2) in colonic mucosa, the composite matrix (carrier) is specifically degraded by colonic coordinated pectic enzymes (e.g., pectate lyase, pectinase) of commensal bacteria at a constant rate (zero-order reaction) to release the active agent; and (3) within the mucosa, released active agent can be selectively transported to the targeted treatment sites to perform specific functions by several pathways, such as:

(a) blood circulation system;

(b) lymphatic system; and (c) mesenteric organ.

The following examples are provided to aid those skilled in the art in practicing the present disclosure.

EXAMPLES

Example 1: Evaluation of the Capped-Spike Protein mRNA of SARS-COV2 in the Pectin/mRNA Hydrogel Composite Particles as an Oral Vaccine in Mice Preparation of Low Methoxyl (LM) Pectin Powder At room temperature, about 100 g of the achenes, pedicels and sepals as a whole were collected from the dry inner shell of female syconium of Jelly fig (*Ficus pumila* var. *awkeotsang*), and put in a filter bag (pore size about 200-400 meshes). Then the loaded bag was kneaded in an anticoagulation extraction solution (sodium citrate solution) for 7 minutes to produce a crude extract. A centrifuge (type: Allegra 21; manufacturer: Beckman Coulter, Inc.) was used to separate the work-in-process Jelly fig LM pectin from the crude aqueous extract for 10 minutes at the speed of 4,500 rpm to remove most impurities. Supernatant was collected and mixed with the same volume of 95% alcohol, and Jelly fig LM pectin floccules were precipitated. A centrifuge (type: Allegra 21; manufacturer: Beckman Coulter, Inc.) was used to remove most of water and the alcohol from the pectin floccules for 10 minutes at the speed of 4,500 rpm, and then the pectin floccules were gently compacted into a block of wet pectin. The wet pectin block was put into an oven, dried at 55° C. and grounded into powder, which had a degree of esterification of about 29.8% and a galacturonic acid content of about 78%, and a molecule weight of 758,300 daltons.

Preparation of Capped-Spike Protein mRNA of SARS-COV2

The capped-spike protein mRNA of SARS-COV was prepared from 2pJET1.2Blunt-SARS-COV2-S plasmid. First, the 2pJET1.2Blunt-SARS-COV2-S plasmids were linearized with Cla I restriction enzyme and purified with Wizard-DNA-Clean-Up-System Kit (Promega). The purified 2pJET1.2Blunt-SARS-COV2-S plasmid DNA (60 μg) was incubated with T7 Reaction Components (included T7 Transcription 5× Buffer 120 μl, 100 mM ATP, CTP, UTP, GTP (each 30 μl) and Enzyme Mix (T7, 60 μl) and with CleanCap@AG (20 μl), for mRNA capping reaction). The aforementioned mixture was supplemented with ddH$_2$O to a total volume of 600 μl. Then, the reaction was divided into 6 PCR tubes, each being 100 μl. After the PCR reaction, the DNase (1 u/ug) was added and incubated for one hour at 37° C. To remove the DNA and protein from the DNase treated mixtures, the Total RNA Extract Kit (Promega) was used to purify the capped spike protein mRNA of SARS-COV. The concentration of the capped spike protein mRNA of SARS-CoV was determined by spectrophotometer in 260/280 nm, and the yield of the capped spike protein mRNA of SARS-COV was about 2 mg.

The pectin/mRNA hydrogel composite particles were obtained by using a water-in-oil (w/o) emulsion method, followed by a phase separation and an in situ precipitation process. Briefly, at room temperature (25° C.), the Jelly fig LM pectin powders (300 mg) were dissolved in water (20 mL) to give a 1.5% (w/v) pectin solution (pH 7.5). The pectin solution (1.5%, 20 mL, pH 7.5) was then mixed with calcium carbonate suspension (500 mM, 1 mL, prepared in 0.1% DEPC-treated water) and an mRNA solution (450 μL of capped spike protein mRNA of SARS-COV@2.0 mg/mL, which gave rise to pectin/mRNA=333:1 (w/w)), and emulsified in canola oil (100 mL) via continuous stirring at a speed of 500-1,000 rpm. After 15 minutes, glacial acetic acid (20 mM)/canola oil (20 mL) was added, and the stirring was continued for another 5 minutes. Due to calcium carbonate dissolved in the acid, the water droplets in oil phase converted into calcium ion crosslinked pectin/mRNA hydrogel composite particle. The emulsion was stirred for another 10 minutes, and then a calcium chloride solution (50 mM, 200 mL) was slowly poured in to achieve phase separation. The upper oil layer was decanted, and the remaining water layer was centrifuged to precipitate the pectin/mRNA hydrogel composite particles, which were washed three times with a calcium chloride solution (50 mM).

Animal Experiments

To evaluate in vivo antibody production after oral delivery administration of the pectin/mRNA hydrogel composite particles, the animals were treated using gavage feeding and blood collection. In the vaccine group (Pectin/mRNA group) and the control group (mRNA-free Pectin group), 8-week-old male C57BL/6 mice (n=3) were fed approximately 5.6 μg at 8 weeks, 10 weeks, and 14 weeks old. As for the obtained mice serum samples, the first three consecutive blood collections were from the submandibular, and the last one was through a cardiac puncture at 15 weeks old, when the mice were sacrificed. Blood samples were further centrifuged and the serum was stored at −80° C. until further immunofluorescence assay (IFA) or western blot analysis was conducted.

IFA

The Sf21 cells were seeded into a 24-well plate ($2\times10^5$ cells/well) and were infected with the recombinant baculovirusvbAc-4E-SARS-COV-2-N-SME with MOI 0.5 for 4 days. The culture medium was discarded, and the well was replenished with fresh medium. The culture was further incubated at 27° C. for 1 hr. The infected Sf21 cells were then fixed with 100 μL of 4% paraformaldehyde solution and washed 4 times with PBS solution. After the fixation, 50 μL of methanol was added to each well, followed by washing the cells four times with PBS. The cells were blocked with 100 μL of 3% bovine serum albumin (BSA) with gentle shaking for 1 hr prior to the addition of the first antibody, which was the mice serum (1:100) or the control anti-S antibodies (1:250). The cells and the first antibody mixture were incubated overnight at 4° C. and washed five times with PBS before the cells were labeled with Alexa Fluor 488-conjugated Affinipure Goat anti-Mouse IgG (H+L) (1:200) and were incubated for another 2 hrs. Lastly, the cells were observed under a fluorescent microscope to analyze the expression of the PCV2-Cap protein in the Sf21 cells.

Figure 2:
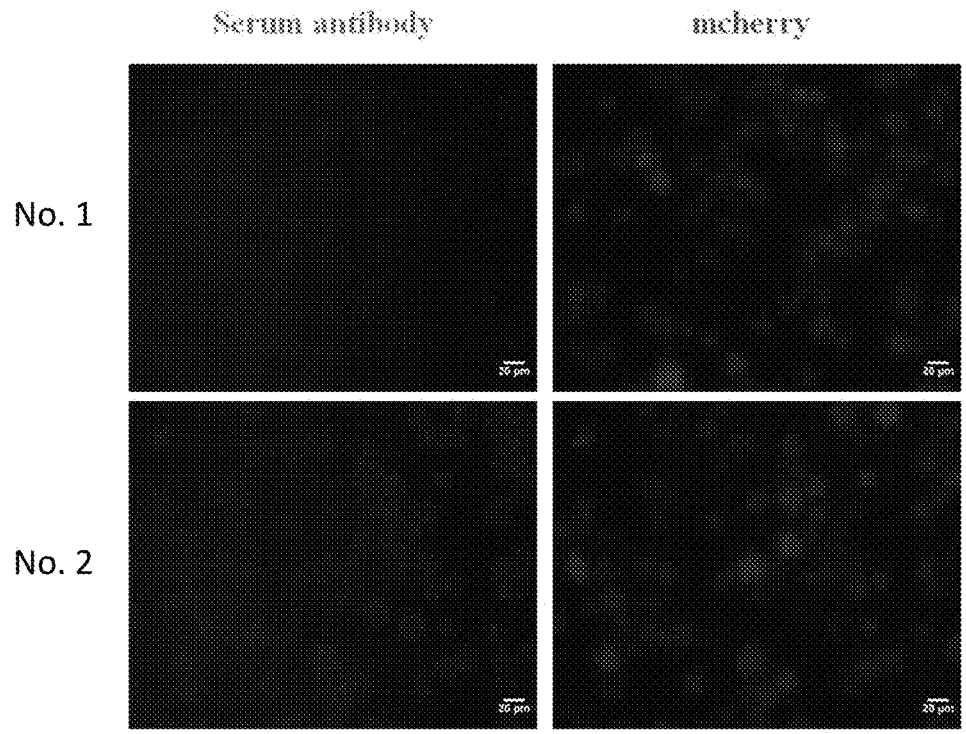
FIG. 2 shows the IFA of serum from the mice at the age of 10 weeks and after first oral vaccination. (A): The two mice were orally administered with the pectin/mRNA hydrogel composites particles; and (B): The two mice were orally administered with the mRNA-free pectin hydrogel particle as control.
Figure 2:
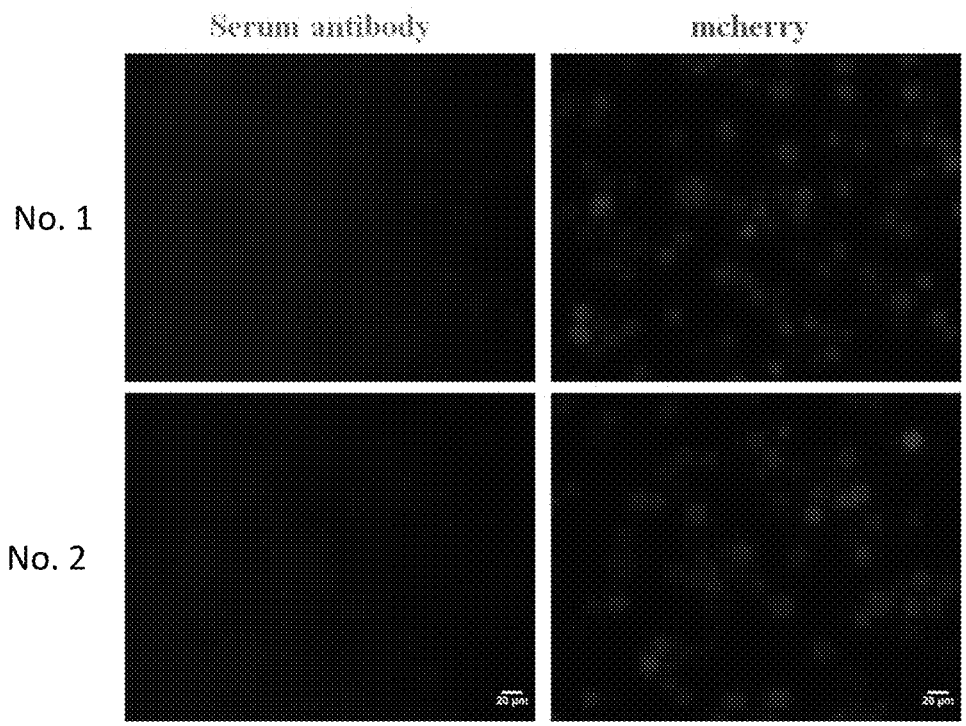
Figure 3:
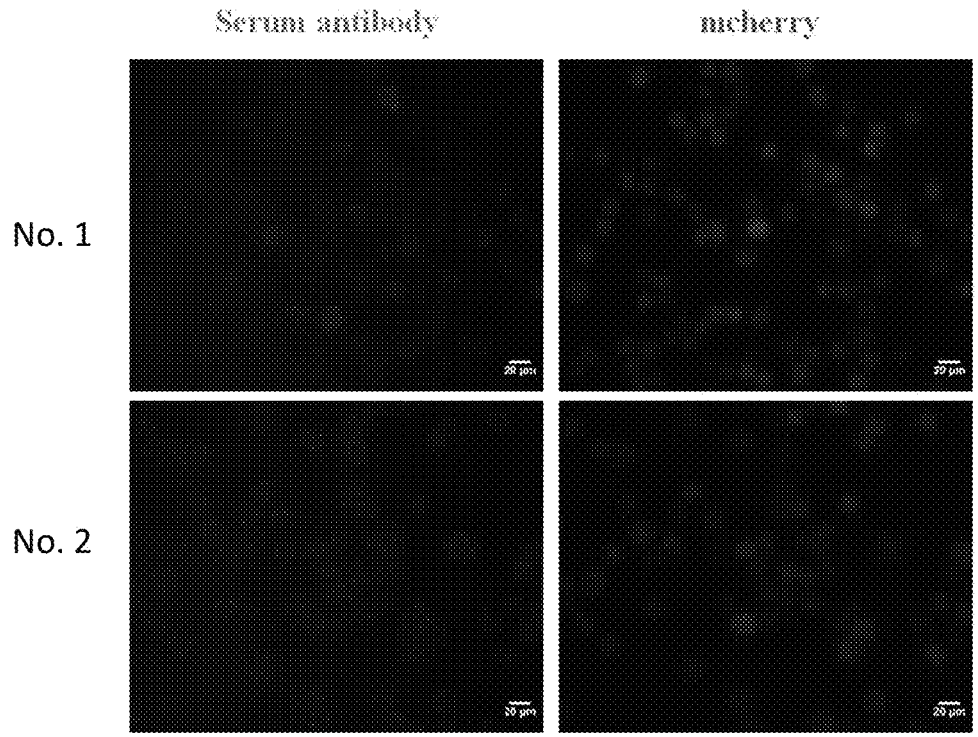
FIG. 3 shows the IFA of serum from the mice at the age of 14 weeks and after the complete oral administration of the three doses of the mRNA vaccine. (A): The two mice were orally administered with the pectin/mRNA hydrogel composites particles; and (B): The two mice were orally administered with the mRNA-free pectin hydrogel particle as control.
Figure 3:
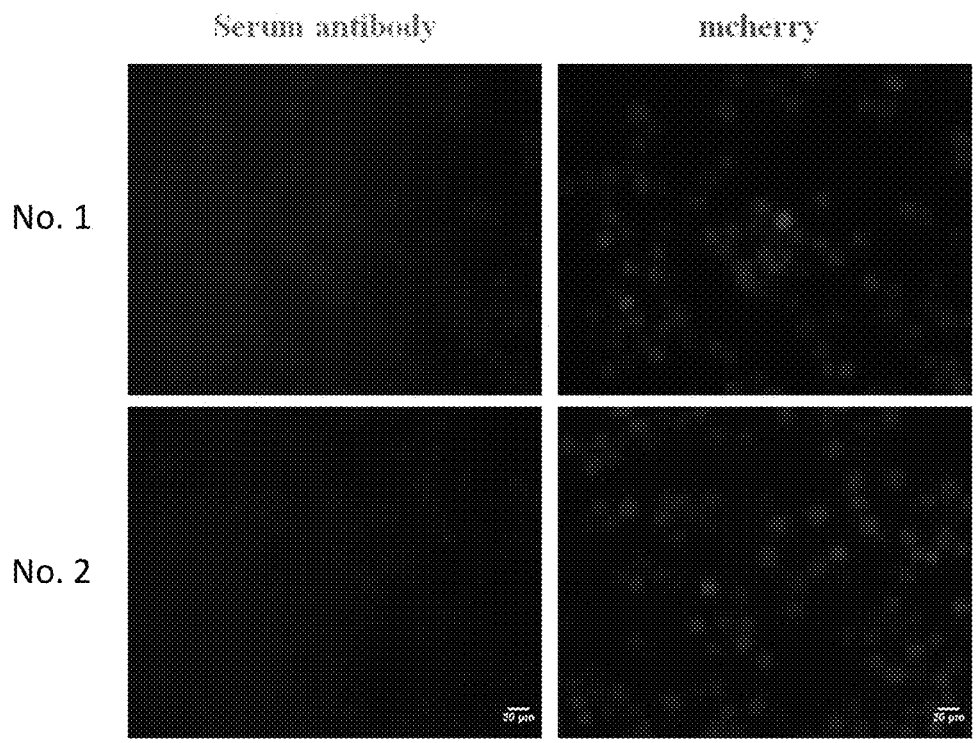
Figure 4:
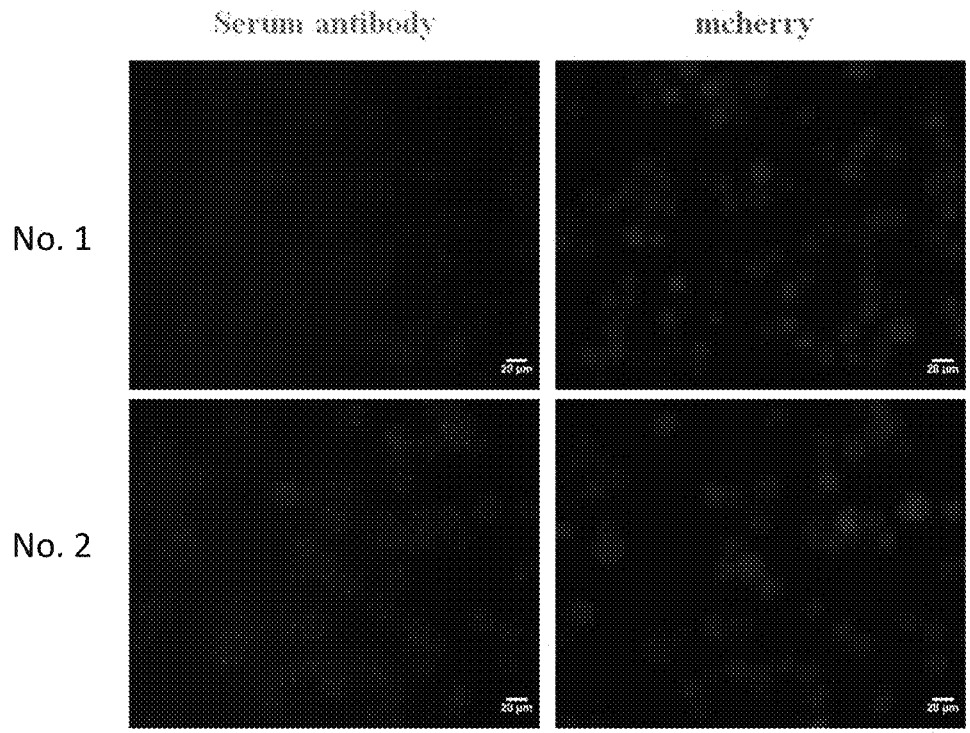
FIG. 4 shows the IFA of serum from the mice at the age of 15 weeks and by the final cardiac puncture. (A): The two mice were orally administered with the pectin/mRNA hydrogel composites particles; and (B): The two mice were orally administered with the mRNA-free pectin hydrogel particle as control.
Figure 4:
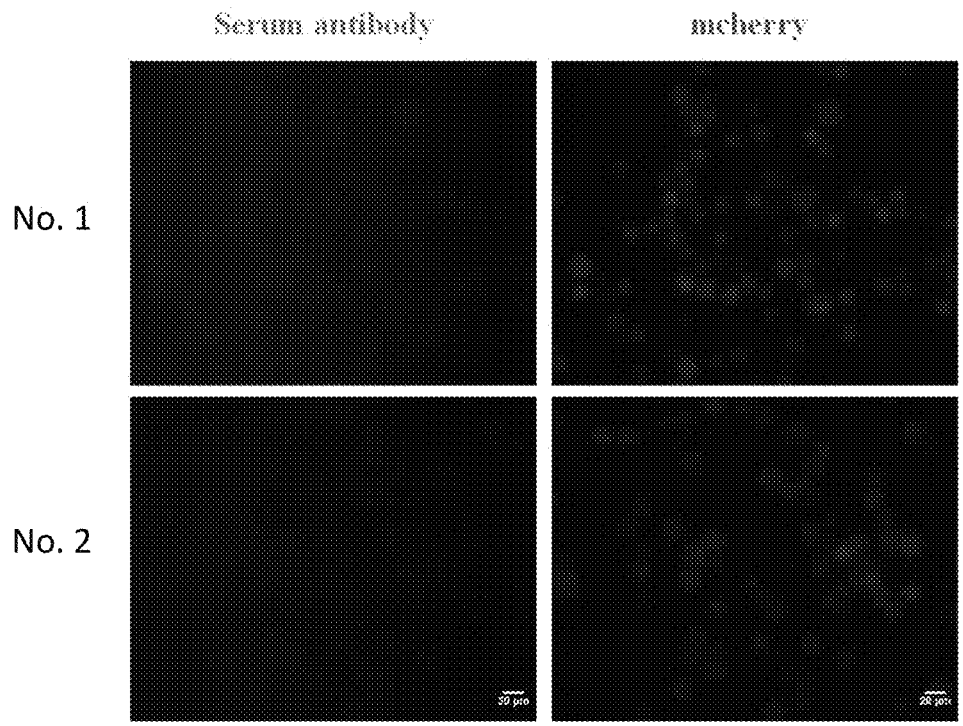

After infection of Sf21 cells with baculovirus vbAc-4E-SARS-COV-2-N-SME, the expression of S protein antigens can be used for IFA to analyze whether the oral administration of the pectin/mRNA hydrogel composites particles can induce antibodies in the experimental mice. Since the baculovirus vbAc-4E-SARS-COV-2-N-SME contains the red fluorescent protein mCherry gene in the chitinase/cathepsin gene locus, the Sf21 cells successfully infected by vbAc-4E-SARS-COV-2-N-SME emitted red fluorescence signals. Secondary antibodies with green fluorescence signals were used to observe whether there was an antibody against the SARS-COV-2-S in serum. From the first serum samples collected from both the Pectin/mRNA group and the control group (mRNA-free Pectin group) before oral administration, the IFA result showed no green fluorescence signal, which indicated that there was no antibody specific to SARS-COV-2-S protein antigen (as shown in FIG. 1). From the second serum samples collected from the Pectin/mRNA group at 10 weeks old, and 2 weeks after the first oral administration, the IFA result showed some faint green fluorescence signals, while the control group (mRNA-free Pectin group) was without the green fluorescence (FIG. 2). From the third serum samples collected from the Pectin/mRNA group at 14 weeks old, and 1 week after complete oral administration of the Pectin/mRNA repeat doses three times in total, the IFA result showed that the Pectin/mRNA group had green fluorescence signals, while the control group (mRNA-free Pectin group) did not have the green signal (FIG. 3). From the fourth serum samples collected from both groups of Pectin/mRNA group and control group (mRNA-free Pectin group) by the final cardiac puncture, the IFA result showed that weakly emitted green fluorescence signals were only found in the Pectin/mRNA group, but not in the control group (FIG. 4). The IFA results showed that the Pectin/mRNA hydrogel composite particles could induce antibodies against the SARS-COV-2 spike protein; therefore, the novel hydrogel composite particles as an oral delivery platform would be competent in the colon-targeted active agent delivery system.

Western Blot Analysis

Figure 5:
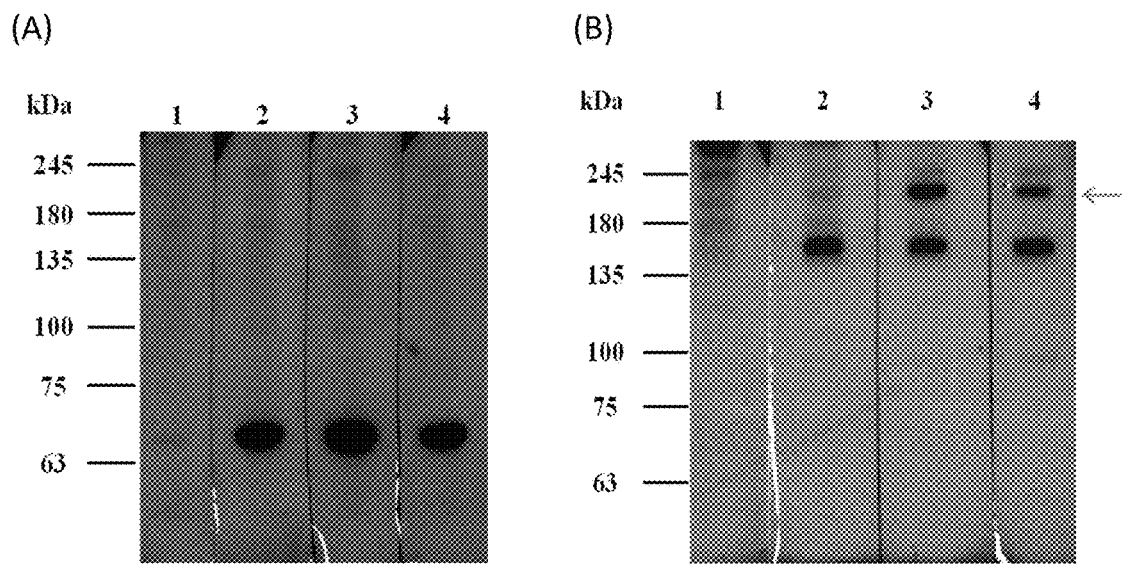
FIG. 5 shows the Western blot of the serum obtained from blood collection at each time point of (A) control group (mRNA-free Pectin group) and (B) oral vaccine group (Pectin/mRNA group). Lane 1: the serum sample before oral administration. Lane 2: the serum sample collected at 2 weeks after oral administration of the first dose. Lane 3: the serum sample collected at 1 week after complete oral administration of 3 doses. Lane 4: the serum sample from final cardiac puncture blood collection (the arrow shows the expected about 180 kDa spike protein of SARS-COV-2). Each serum sample was diluted at a ratio of 1:1,000. The anti-mouse IgG HRP-linked antibody is used as the secondary antibody, and the dilution ratio is 1:10,000.

To further confirm the aforementioned IFA results, we conducted Western blot to analyze the serum samples used in the IFA experiments. To produce the SARS-COV-2-S (approximately 180 kDa) as an antigen used in the western blot analysis, the cell lysate of vbAc-4E-SARS-2-N-SM infected Sf21 cells was collected and the serum samples of the experimental mouse were used as primary antibodies to conduct the immunoblots. None of the serum samples collected from the control group (mRNA-free Pectin group) could detect the about 180 kDa spike protein of SARS-CoV-2 (FIG. 5(A)) in Western blot. In contrast, the Western blot of the serum collected from the Pectin/mRNA group did detect the expected about 180 kDa spike protein of SARS-COV-2 (FIG. 5(B)). From all the serum samples collected from the Pectin/mRNA group, the band signal of about 180 kDa was found in the third and fourth serum samples, but not the first and second ones that were collected after complete oral administration of the Pectin/mRNA repeat doses, three times in total. The Western blot results further showed that the oral administration of the Pectin/mRNA hydrogel composite particles could induce antibodies against the SARS-COV-2 spike protein; therefore, the novel hydrogel composite particles as an oral delivery platform would be competent in the colon-targeted active agent delivery system.

Example 2: Fabrication and Characterization of Pectin/Insulin Hydrogel Composite Particles Animals Non-obese diabetic (NOD) C57BL/6 mice (each group of 2 mice, each weighted about 20-25 g, about 8 weeks old) were used in the present study. NOD mice were provided by the (Taiwan) National Laboratory Animal Center (NLAC, Taiwan). They were housed and maintained in individually ventilated cages throughout the study in the animal facility with controlled temperature (20-26° C.), humidity (40-70%) and a 12 hrs/12 hrs light/dark cycle (light on at 7:00 a.m.) with food and water provided ad libitum.

NOD Mice and Treatment

The non-fasting blood glucose level of each mouse was measured daily. Diabetes onset was defined by two successive readings of non-fasting blood glucose >250 mg/dL. Mice in the test group were gavage fed with the present pectin/insulin hydrogel composite particles (3.3 mg/Kg) once per day, while the mice in the control group received Insulin-free pectin hydrogel particles (i.e., without insulin), and blood glucose levels were measured at time points of 0, 30, 60, 90, 120, 150, 180, 210, and 240 minutes from the tail vein with a Roche-Check Performa blood glucose analyzer. The behaviors, activities, food and water intakes, etc., of the mice were observed daily throughout the entire study.

Fabrication of Pectin/Insulin Hydrogel Composite Particles

The pectin/insulin hydrogel composite particles were prepared with 1.5, 3, or 6% pectin solution in accordance with the procedures described in Example 3, except that the DNA solution was replaced by an insulin solution (20 mg/mL, 250 µL), and the thus-produced pectin/insulin hydrogel composite particles were freeze-dried and analyzed for their respective loads of insulin therein. Results are summarized in Table 1.

TABLE 1

The content of insulin loaded in the pectin/insulin hydrogel composite particles (in powder form)

| | Conditions | | | |
|---|---|---|---|---|
| Pectin (%) | 1.5 | 3 | 6 | 6 |
| Stirred Speed (rpm) | 1,000 | 1,000 | 500 | 1,000 |
| Insulin (mg) | 5 | 5 | 5 | 5 |
| Insulin content in the hydrogel composite particles (µg/mg) | 1.73 ± 0.13 | 32.77 ± 3.17 | 103.85 ± 4.16 | 9.06 ± 1.10 |

According to the data in Table 1, the pectin/insulin hydrogel composite particles produced with 6% pectin solution and continuously stirred at the speed of 500 rpm gave rise to the composite particles having the highest load of insulin, which was 103.85±4.16 µg of insulin per mg of hydrogel composite particles.

Blood Glucose Level (BGL) in NOD Mice

Figure 6:
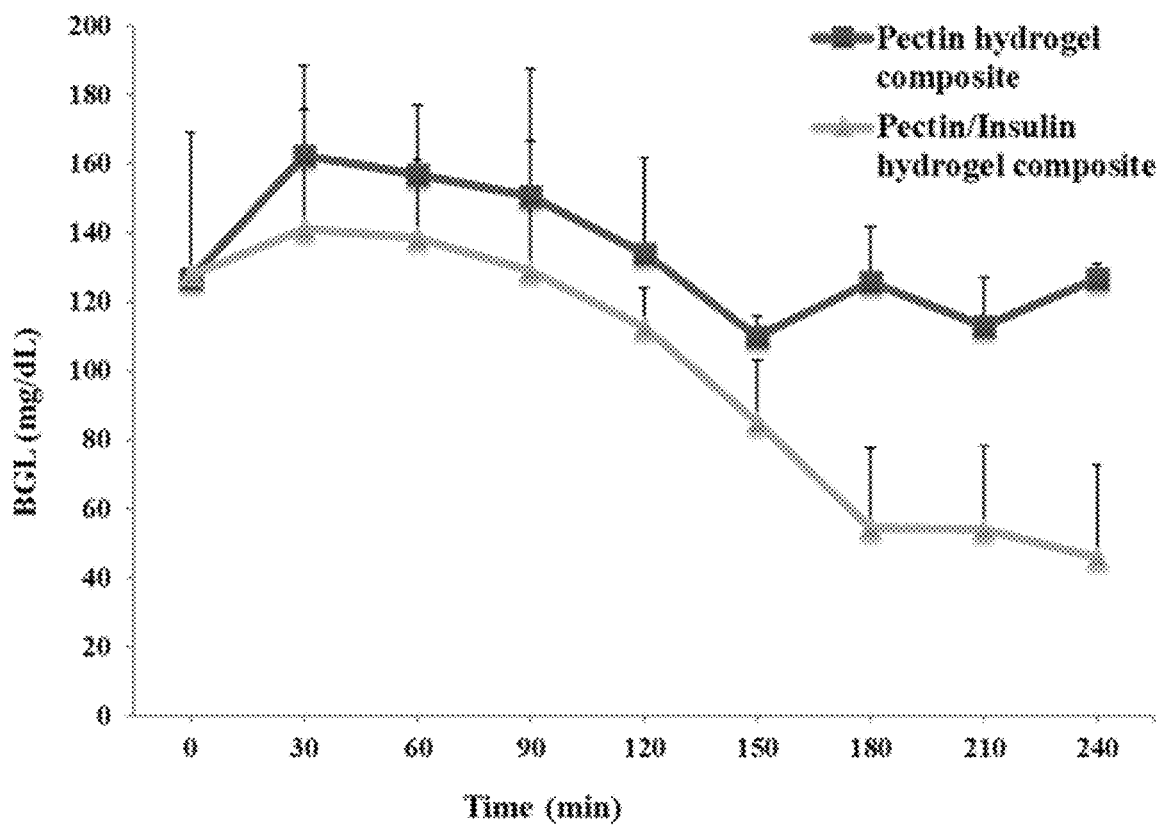
FIG. 6 shows the blood glucose level (BGL) in the NOD mice of the control group (Insulin-free Pectin group) and the oral Insulin group (Pectin/Insulin group).

The pectin/insulin hydrogel composite particles produced with 6% pectin solution at the stirring speed of 500 rpm were gavage fed to NOD mice (n=43) at the dose of 3.3 mg/Kg, while the control mice (n=3) received Insulin-free pectin hydrogel particles, and blood glucose levels were measured at time points of 0, 30, 60, 90, 120, 150, 180, 210, and 240 minutes from the tail vein with a Roche-Check Performa blood glucose analyzer. Results are illustrated in FIG. 6.

The control group of diabetic mice that received Insulin-free pectin hydrogel particles retained a relatively high blood glucose level at about 125 mg/dL throughout the entire experimental period (240 minutes); in contrast, due to pectin/insulin hydrogel composite particles received, the experimental group of diabetic mice had a continuous decline from about 125 mg/dL to about 60 mg/dL in blood glucose levels from the 90 minute mark until the end of the 240 minute period. Due to gavage feeding, the stress-induced increase in blood glucose levels from 0 to 90 minutes was negligible (Chang, 2013, *Pattern of Stress-Induced Hyperglycemia according to Type of Diabetes: A Predator Stress Model*). The results showed that the Pectin/insulin hydrogel composite particles via oral pathway could effectively lower blood glucose levels in diabetic mice; therefore, the novel Jelly fig LM pectin hydrogel composite particles as an oral delivery carrier platform would be competent in the colon-targeted active agent delivery system.

Example 3: Fabrication and Characterization of Pectin/DNA Hydrogel Composite Particles 3.1: Fabrication of Pectin/DNA Hydrogel Composite Particles The pectin/DNA hydrogel composite particles were fabricated by a water-in-oil (w/o) emulsion method and in situ precipitation; the processes are briefly described as follows:
(a) providing an aqueous phase (25 mL in total) including a pectin solution (20 mL, 1.5%, 300 mg Jelly fig LM pectin powder used), a DNA suspension (4 mL) and a calcium carbonate suspension (1 mL), comprising:
  (a1) providing a solution at pH of about 7.5 and containing the above Jelly fig LM pectin and the DNA suspension (4,000 µL of pCMV-EGFP-N1 plasmid@0.5 mg/mL, which gave rise to pectin 300 mg: DNA 2 mg (4,000 µL, 0.5 mg/mL)=150:1 (w/w) with the DNA encapsulation efficiency of 28.2%) (data not shown); and
  (a2) mixing a suspension containing calcium carbonate (500 mM, 1 mL) with the above solution;
(b) providing canola oil as an oil phase (100 mL), and mixing the oil phase with the above aqueous phase (25 mL) and continuously stirring at a speed of 500 rpm to form a water-in-oil emulsion (w/o emulsion);
(c) after 15 minutes, dripping a 20 mM glacial acetic acid-added canola oil (20 mL) into the w/o emulsion, and stirring for another 5 minutes, such that the acid dissolves calcium carbonate to release calcium ions in water, thus forming calcium ion-crosslinked pectin hydrogel particles with DNA embedded therein;
(d) slowly pouring a critical volume of the calcium chloride solution into the w/o emulsion, resulting in the following:
  (d1) reinforcing the hydrogel composite particles by calcium ions in the external medium; and
  (d2) inducing demulsification and breaking the w/o emulsion into two layers of the lower-layer aqueous phase and the upper-layer oil phase, wherein the DNA-loaded hydrogel composite particles remained in the lower-layer aqueous phase;
(e) decanting the upper oil layer, centrifuging the lower-layer aqueous phase to precipitate the pectin/DNA hydrogel composite particles, which were collected and washed three times with a calcium chloride solution (50 mM); and
(f) collecting the pectin/DNA hydrogel composite particles by filtering through a 0.45 µm filter.

Figure 7:
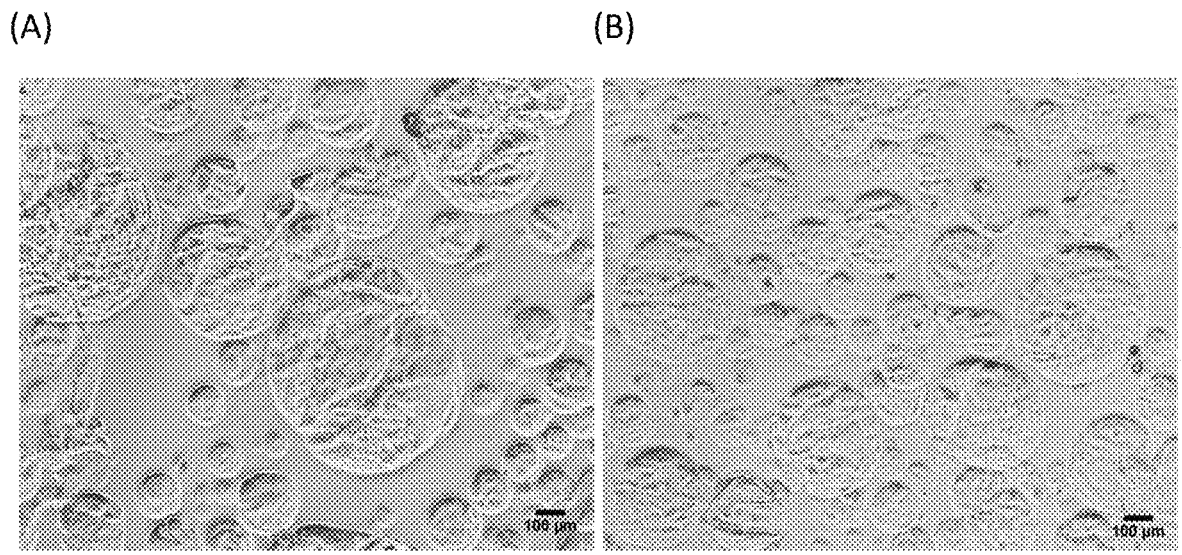
FIG. 7 shows the optical images of the pectin/DNA hydrogel composites particles. (A): Pectin/DNA=150:1; (B): Pectin/DNA=1,500:1.
Figure 8:
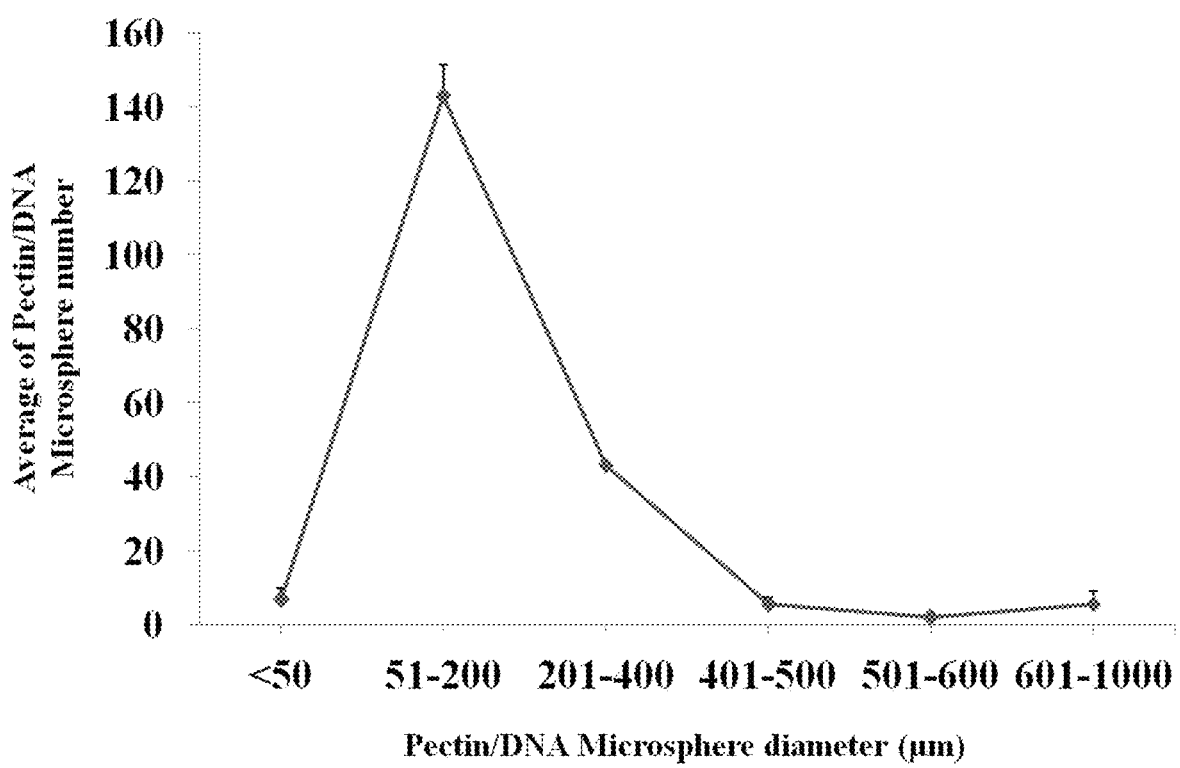
FIG. 8 shows the size analysis of the wet pectin/DNA hydrogel composite particles.

Optical images revealed that the thus-produced wet pectin/DNA hydrogel composite particles (Pectin:DNA=150:1) were independently in spherical shapes (FIG. 7). Size analysis revealed that the wet pectin/DNA hydrogel composite particles have a size of about 20 µm to about 1,000 µm (FIG. 8), with a major population being a size of about 51 µm to about 200 µm, and a second major population being a size of about 201 µm to about 400 µm.

Figure 9:
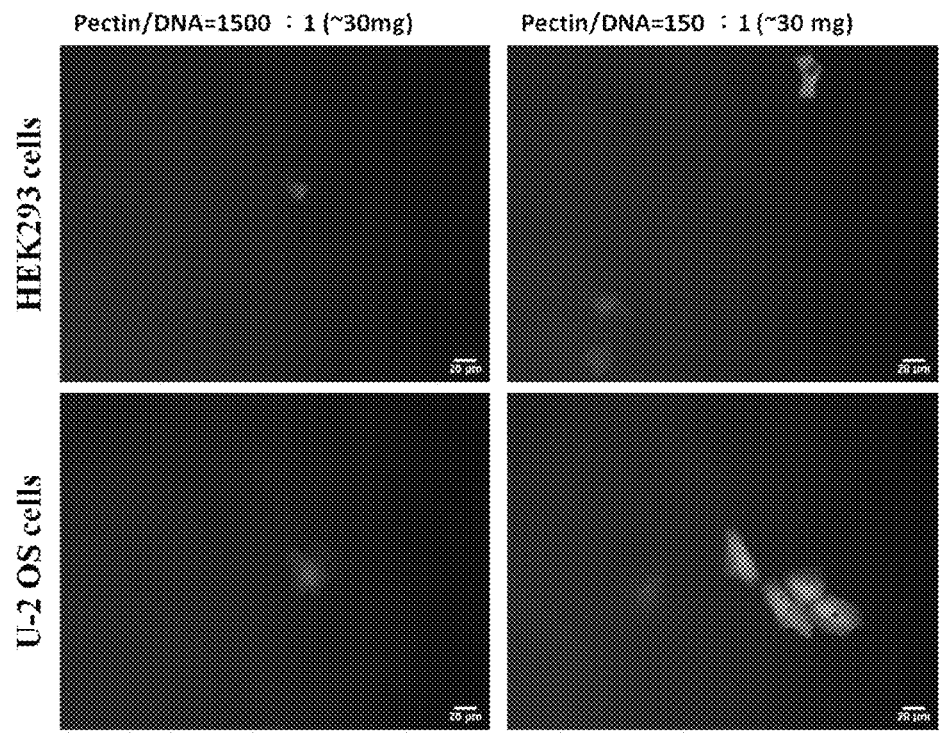
FIG. 9 shows the transfection ability analysis of the pectin/DNA hydrogel composite particles.
Figure 10:
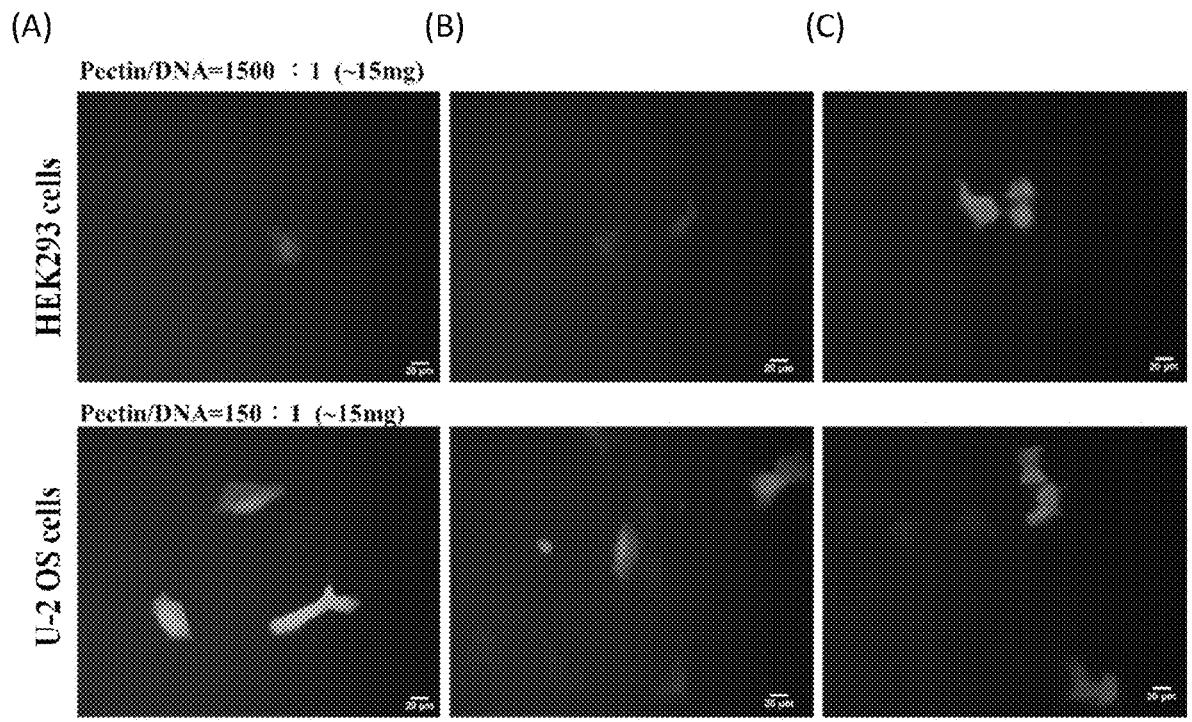
FIG. 10 shows the transfection ability analysis of the pectin/DNA hydrogel composite particles after being stored at 26° C. for (A) 1 day, (B) 17 days, and (C) 30 days.

3.2: Transfection Ability Shelf Life of Pectin/DNA Hydrogel Composites Particles To assess the transfection ability of DNA loaded in calcium ion-crosslinked pectin hydrogel composite particles produced by the above method in 3.1, human bone osteosarcoma epithelial cells (U2OS) and human embryonic kidney cells (HEK293) were used in a lab test. The cells were seeded in 24-well plates ($1 \times 10^5$ cells/well) and cultured in DMEM medium supplemented with 5% fetal bovine serum (FBS) at 37° C., 5% $CO_2$ for at least 16 hours. The cells were treated with the pectin/DNA hydrogel composite particles (100 mg/mL, 300 µL) for 24 hrs, and then the cells were returned to culture. After 48 hrs, cells were examined under fluorescence microscope, and the presence of green fluorescent EGFP in the cells indicated that the EGFP DNA encapsulated in the pectin/DNA hydrogel composite particles was successfully delivered to and expressed in U2OS or HEK293 cells (FIG. 9), among which cells transfected with the pectin/DNA hydrogel composite particles (Pectin:DNA=150:1) gave the strongest fluorescent signals. Interestingly, after being stored at 26° C. (room temperature) for 30 days, these wet pectin/DNA hydrogel composite particles remained available for transfection purposes (FIG. 10).

3.3: Size Distribution of the Freeze-Dried Pectin/DNA Hydrogel Composite Particles After the wet pectin/DNA hydrogel composite particles were obtained from the above method in 3.1, they could be further treated into a powder form by freeze drying (lyophilization).

Figure 11:
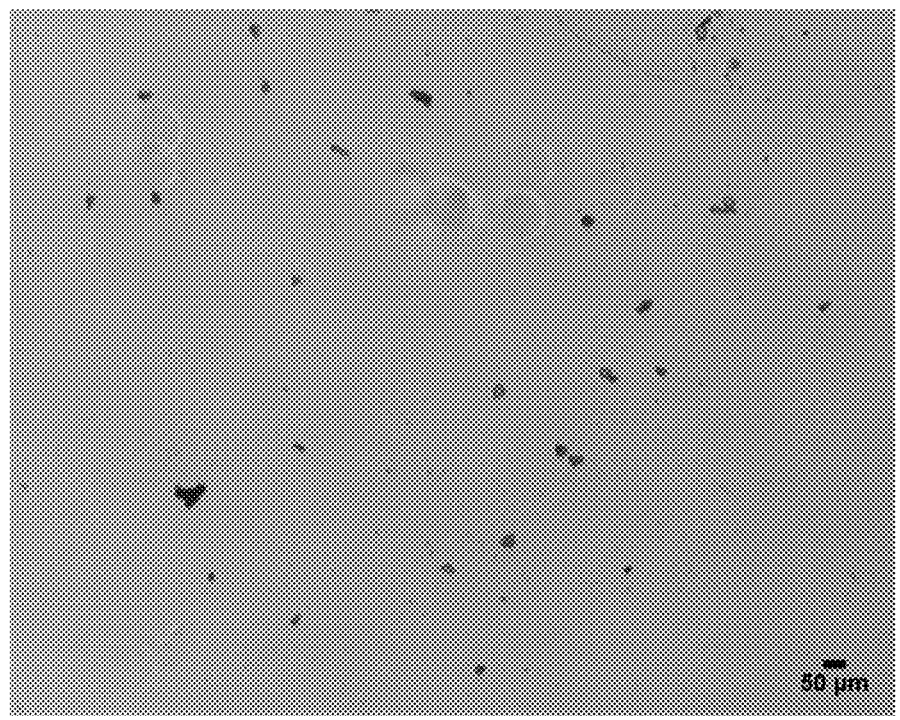
FIG. 11 shows (A) the freeze-dried pectin/DNA hydrogel composite particles under a microscope; and (B) the particle size distribution thereof.
Figure 11:
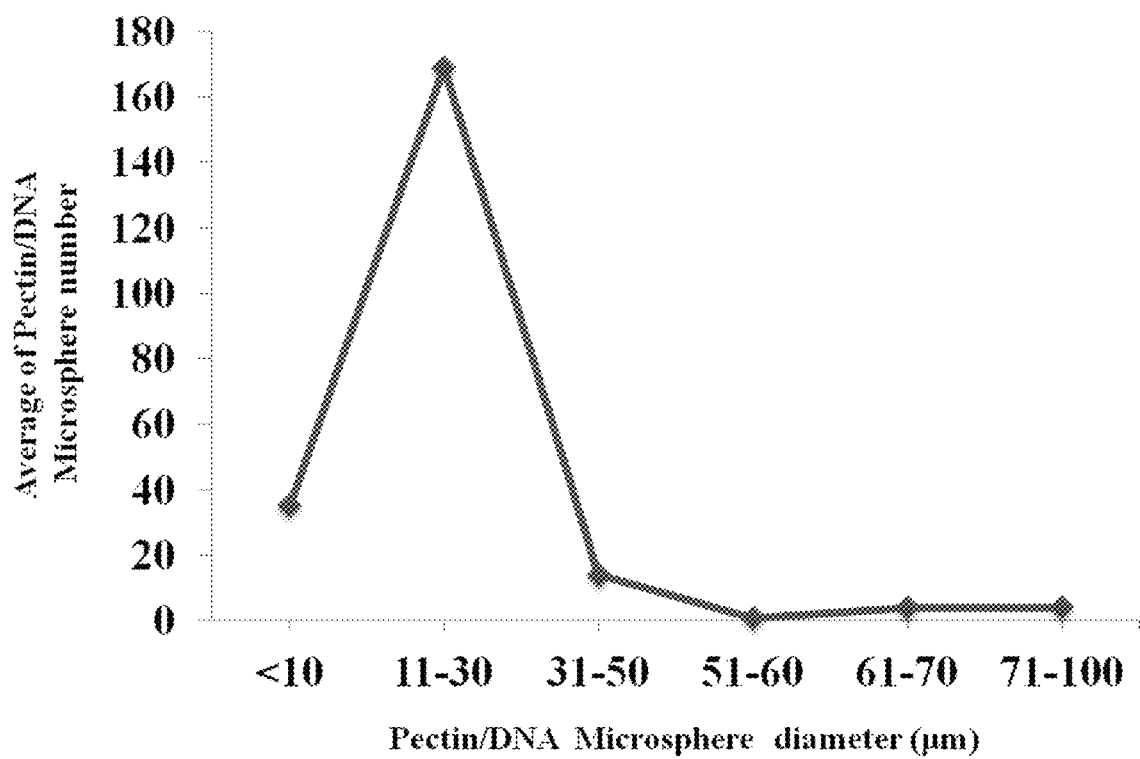

First, the wet pectin/DNA hydrogel composite particles were placed in a −80° C. refrigerator for at least one day, and then freeze-dried into the powder form. From observation under a microscope, an image from a fraction of the powder is seen in FIG. 11(A), and a particle size distribution curve is shown in FIG. 11(B). The overall particle size distribution of the freeze-dried powder form was between 5-100 µm, while the most abundant particle diameter in the subdivision population was about 11-30 µm.

Example 4: The Enzyme-Catalyzed Surface Erosion of Calcium Ion-Crosslinked Pectin Hydrogel Composite Particles Could Be Used for Zero Order Reaction Administration In order to show that the above calcium ion-crosslinked pectin hydrogel particles can release their load in a constant rate of zero-order reaction by surface erosion of enzyme catalysis, the pectin/Coomassie Blue R250 hydrogel composite particles were fabricated by a water-in-oil (w/o) emulsion method and in situ precipitation, and the processes are briefly described as follows:
(a) providing an aqueous phase including the pectin solution, Coomassie Blue R250 solution and 500 mM calcium carbonate suspension, including:
  (a1) providing 80 mL solution at pH of about 7.5, containing 2,400 mg Jelly fig LM pectin (3% (w/v)); and 20 mg Coomassie Blue R250 dissolved in 1 mL of reverse osmosis water; and
  (a2) dividing the above 80 mL of Jelly fig LM pectin solution into 4 aliquots (each 20 mL) and adding 1 mL of 500 mM calcium carbonate aqueous solution to each of them, and stirring well;
(b) adding 37.5, 75, 150 and 300 µl of the above Coomassie Blue R250 solution at a concentration of 20 mg/mL separately to the above 4 aliquots (each 20 mL) of the mixture solution, and stirring and mixing well;

(c) mixing each of the above solutions (as the aqueous phase, about 20 mL each) separately with canola oil (100 mL) via continuous stirring at a speed of 1,000 rpm to form a water-in-oil emulsion (w/o emulsion);

(d) adding 20 mL of canola oil containing 80 mM glacial acetic acid into each of the above water-in-oil emulsion (w/o emulsion) under continuous stirring at a speed of 900 rpm for 5 minutes;

(e) slowly pouring 50 mM aqueous calcium chloride solution along the wall into each beaker under continuous stirring until the mixture reaches an upper edge of the beaker, and then phase separation occurred via stirring at 1,000 rpm for 10 minutes;

(f) removing the oil phase in the upper layer of each mixture, and centrifuging the aqueous phase at 4,500 rpm for 1 minute to precipitate the particles;

(g) removing the supernatant, and washing the particles three times with a 50 mM calcium chloride aqueous solution;

(h) removing the aqueous solution of calcium chloride with a 0.45 μm filter to obtain wet particles.

Figure 12:
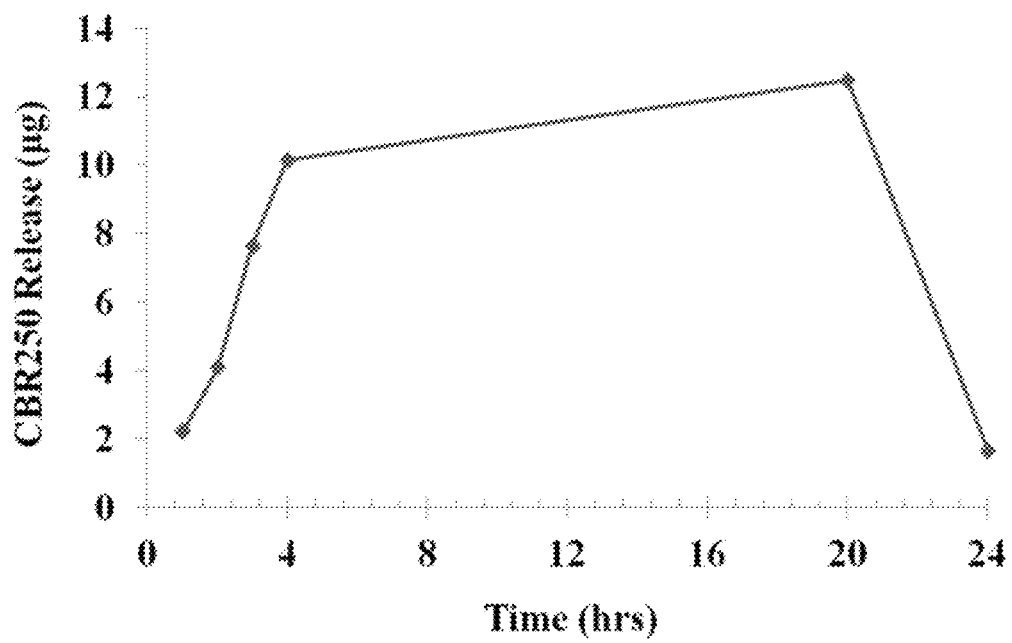
FIG. 12 shows the release of Coomassie Blue R250 in pectin hydrogel composite particles over time. (A): 1, 2, 3, 4, 20, and 24 hours; (B): 1, 2, 3, and 4 hours.
Figure 12:
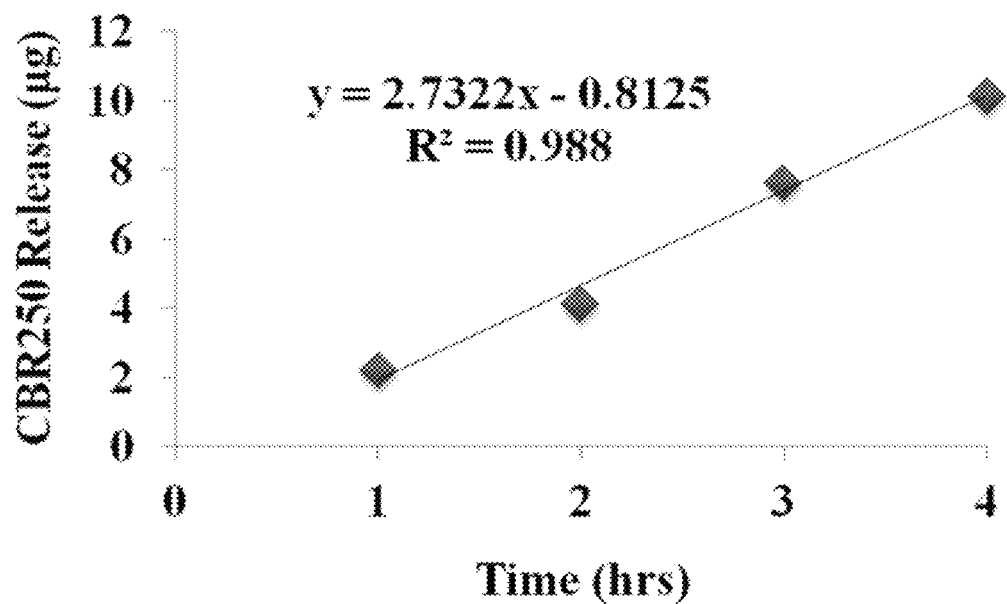

The 500 mg of pectin/Coomassie Blue R250 hydrogel composite particles were mixed with 5 mL of Pectinex solution (4%, pH 3.0) at 55° C. After 1, 2, 3, 4, 20 and 24 hrs of incubation, the mixture was centrifuged, and the aliquot (about 200 μL) of the upper clear solution was taken out. The Coomassie Blue R250 level therein was determined by measuring the absorption at 595 nm (OD595) using a spectrophotometer. Results are illustrated in FIG. 12(A). The results indicated that in the first 20 hours, the release of Coomassie Blue R250 increased gradually. However, the release of Coomassie Blue R250 dropped dramatically after 24 hours. This may imply that the activity of Pectinex can be sustained for about 20 hours but diminishes thereafter. Interestingly, as shown in FIG. 12(B), the release of Coomassie Blue R250 is a nearly linear increase in time ($R^2$=0.988). This result indicated that the release rate of Coomassie Blue R250 from the pectin hydrogel composite particles is constant and belongs to zero order reaction kinetics.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

What is claimed is:

1. A method for manufacturing hydrogel composite particles, consisting of:
   (a) providing an aqueous phase consisting essentially of a Jelly fig low methoxyl pectin, an active agent and an insoluble salt of calcium; wherein the Jelly fig low methoxyl pectin has the characteristics of:
      (1) an average molecular weight of at least 750,000 daltons;
      (2) an esterification degree of about 31% or less; and
      (3) a galacturonic acid content of at least 75% to about 90%;
   (b) mixing the aqueous phase with an oil phase to form a water-in-oil emulsion;
   (c) dripping an acid into the water-in-oil emulsion, such that the insoluble salt of calcium dissolves to release calcium ion, and the Jelly fig low methoxyl pectin crosslinks with calcium ion to form hydrogel composite particles containing the active agent;
   (d) pouring a critical volume of an aqueous solution consisting essentially of a soluble salt of calcium into the water-in-oil emulsion to solidify the hydrogel composite particles and to de-emulsify the water-in-oil emulsion into the aqueous phase and the oil phase, wherein the hydrogel composite particles are in the aqueous phase;
   (d1) decanting the oil phase; and
   (e) separating the hydrogel composite particles from the aqueous phase by centrifugation or filtration, wherein the hydrogel composite particles consists essentially of calcium pectinate, the active agent and water.

2. The method of claim 1, wherein the oil phase in (b) is selected from the group consisting of canola oil, corn oil, peanut oil, sunflower oil, soybean oil, olive oil, linseed oil and palm oil.

3. The method of claim 1, wherein the acid in (c) is selected from the group consisting of acetic acid, citric acid, phosphoric acid, hydrochloric acid and nitric acid.

4. The method of claim 1, wherein the active agent is selected from the group consisting of nucleic acids, peptides, proteins, therapeutic agents, diagnostic agents, non-biological materials, and combinations thereof.

5. The method of claim 1, wherein the active agent is blood or blood components, an allergen, a cell, or a tissue.

6. The method of claim 1, wherein the active agent is a somatic cell, a probiotic, a chimeric antigen receptor T cell, insulin, or a CRISPR/Cas polynucleotide.

* * * * *